US008445411B2

(12) United States Patent
Bodmer et al.

(10) Patent No.: US 8,445,411 B2
(45) Date of Patent: *May 21, 2013

(54) DETECTION OF CIRCULATING TUMOR CELLS IN PERIPHERAL BLOOD WITH AN AUTOMATED SCANNING FLUORESCENCE MICROSCOPE

(75) Inventors: Sir Walter Bodmer, Oxford (GB); Triantafyllos P. Tafas, Rocky Hill, CT (US); Michael Kilpatrick, West Hartford, CT (US); Petros Tsipouras, Madison, CT (US); Xiuzhong Wang, Hamden, CT (US); Youngmin Kim, Wallingford, CT (US); Michael Thomas, West Hartford, CT (US); Antti Seppo, Bronx, NY (US); Triantafyllia Ntouroupi, Athens (GR); Changhua Yu, Hamden, CT (US); Charles Climer, Cheshire, CT (US)

(73) Assignee: Ikonisys, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/337,823

(22) Filed: Dec. 27, 2011

(65) Prior Publication Data

US 2012/0094868 A1 Apr. 19, 2012

Related U.S. Application Data (63) Continuation of application No. 12/270,820, filed on Nov. 13, 2008, now Pat. No. 8,088,715.

(60) Provisional application No. 61/002,836, filed on Nov. 13, 2007.

(51) Int. Cl.
C40B 30/04 (2006.01)

(52) U.S. Cl.
USPC .................................................. 506/9; 382/134

(58) Field of Classification Search
USPC ........................ 506/9; 435/29, 629; 382/134
See application file for complete search history.

(56) References Cited

U.S. PATENT DOCUMENTS

| 2005/0136549 A1* | 6/2005 | Gholap et al. ............... 436/501 |
| 2005/0173632 A1* | 8/2005 | Behar et al. .................. 250/311 |
| 2007/0025915 A1* | 2/2007 | Cuttitta et al. .............. 424/1.49 |
| 2007/0099209 A1* | 5/2007 | Clarke et al. ...................... 435/6 |
| 2007/0269432 A1* | 11/2007 | Nakamura et al. ......... 424/138.1 |
| 2007/0269845 A1* | 11/2007 | Bjerkvig ........................ 435/29 |
| 2008/0014590 A1* | 1/2008 | Dahary et al. ..................... 435/6 |
| 2008/0248499 A1* | 10/2008 | Chiu et al. ................... 435/7.23 |
| 2008/0254480 A1* | 10/2008 | Vujanovic ..................... 435/7.1 |
| 2008/0254481 A1* | 10/2008 | Love et al. ..................... 435/7.1 |
| 2008/0269067 A1* | 10/2008 | Semizarov et al. ............... 506/9 |
| 2010/0040637 A1* | 2/2010 | Van Orden et al. ......... 424/172.1 |

* cited by examiner

*Primary Examiner* — Nathan Ha (74) *Attorney, Agent, or Firm* — Kelley, Drye and Warren LLP (57) ABSTRACT

An automated, highly sensitive, specific and potentially quantitative detection method using an automated microscope for identifying and enumerating rare cancer cells in blood and other fluids.

9 Claims, 7 Drawing Sheets

DETECTION OF CIRCULATING TUMOR CELLS IN PERIPHERAL BLOOD WITH AN AUTOMATED SCANNING FLUORESCENCE MICROSCOPE

CROSS REFERENCE TO RELATED APPLICATIONS

This application is a continuation application of U.S. patent application Ser. No. 12/270,820, filed Nov. 13, 2008, which claims the benefit of priority of U.S. Provisional Application No. 61/002,836, filed Nov. 13, 2007. This reference and all additional references cited in this specification, and their references, are incorporated by reference herein in their entirety.

1. BACKGROUND OF THE INVENTION

1. Field of the Invention

The present invention generally relates to an automated method for detecting circulating cancer cells in an individual. There is presented in one embodiment a method of assessing treatment protocols in the treatment of one or more cancers.

2. Description of the Related Art

Primary tumor cells presumably spread to other organs via blood and lymphatic circulation (1), and are probably shed from tumors at all stages, often well before metastasis. Circulating tumor cells (CTC) are likely to reflect both tumor cell bulk and tumor growth (2, 3).

Identification and counting CTC when they are very rare (at most a few CTC per ml) could be an indication of a cancer, or even of a precancerous growth before the appearance of evident clinical symptoms. The potential interest in the detection of CTC in peripheral blood was first suggested over a century ago (4) but because of their very low numbers, CTC cannot be detected by conventional methods. The challenge is to develop an approach that combines high sensitivity with high specificity for the identification and characterization of rare tumor cells circulating in the blood enabling them to be distinguished from normal epithelial cells and leukocytes.

Clear-cut detection of circulating tumor cells could facilitate cancer prognosis, diagnosis of minimal residual disease, assessment of tumor sensitivity to anticancer drugs, and personalization of anticancer therapy. A highly sensitive and specific identification of CTC could also have a potential application in the early diagnosis and screening of invasive cancers.

Tumor cells, epithelial cells, platelets and mononuclear white cells have been enriched from whole blood, and specifically separated from neutrophils and erythrocytes, by a variety of approaches including immunomagnetic separation, density gradients and filtration (10-13). The separated cells can then be collected for cytopathological analyses, immunolabelling and molecular studies. Various methods have been used for the detection and enumeration of CTC. These include flow cytometry, nucleic acid based approaches (RT-PCR, methylation specific PCR) and immunofluorescence microscopy (4-9).

RT-PCR based methods analyze the expression of genes specific to epithelial cells or to the normal tissues from which the tumor cells originate. The main potential advantage of this approach is its high sensitivity. However, since cell integrity is destroyed during RNA extraction, this approach precludes the analysis of cell morphology and phenotype and so, in particular, may not be able to distinguish material shed directly from normal tissue as opposed to from tumors nor does it allow the detection of several associated changes in the same cell. RT-PCR tests thus do not enable counting of CTC and can, in general, only give a positive or negative response that depends on the sensitivity of the test and on the amount of blood that can be tested. In addition, RT-PCR tests cannot distinguish between circulating normal and cancer cells since they nearly always detect tissue-specific and not cancer-specific mRNAs in peripheral blood (14, 15).

Immunofluorescence microscopy enables analysis of cell morphology and direct counting of identifiable presumptive tumor cells. Detection is carried out by immunolabeling of cells using appropriate antibodies. However, since there are so far no antibodies for tumor specific antigens, antibodies specific to epithelial antigens have been used to identify CTC, for example, EpCAM, BerEP4, and epithelial specific Cytokeratins (16-19). Other markers that are not necessarily specific to epithelial cells have also been used. These include antibodies to mammaglobin, PSA, CEA, surviving and HER-2 (8, 20). However, false negative results can occur since these antigens are not present in all tumor cells. Despite these difficulties, the literature in general shows the presence of increasing numbers of CTC in patients having more advanced cancers, higher risk of relapse and poor prognosis (4, 21-23).

There is a need therefore for a highly sensitive, reliable, and quantitative detection method for CTC in the blood that overcomes the short comings of prior methods.

2. SUMMARY OF THE INVENTION

Various embodiments are disclosed herein.

In one embodiment, an automated method of detecting circulating tumor cells in fluids obtained from patients and generating information used for diagnosis and/or monitoring therapeutic progress comprising the steps of
  a) obtaining fluid from an individual;
  b) partially purifying tumor cells in fluid;
  c) contacting partially purified tumor cells with one or more distinguishable labeled probes directed to one or more characteristic features predetermined to distinguish tumor cells from normal cells; wherein the labeled probe(s) are contacted with said characteristic feature under conditions to sufficiently affix labeled probe to withstand processing;
  d) automatically obtaining a representation of one or more distinguishable labels;
  e) automatically analyzing the distribution and intensity of binding of the one or more labels in the representation to determine the presence of a cancer cell;
  f) automatically reporting results of the analysis of step (e); wherein steps d-f are carried out without intervention by a human.

3. BRIEF DESCRIPTION OF THE FIGURES

FIG. 1A shows a high magnification target gallery screen displaying images of identified C32 cells. FIG. 1B displays one of the target C32 cells at high magnification.

4. DEFINITIONS

As used herein, "tag" and "label" relate synonymously to a moiety conjugated to a probe to render the probe detectable by a particular detection method and modality.

By "probe" it is meant to reference a substance specifically designed to bind to a cellular target, and not to bind significantly to cellular moieties or structures not intended to be a target. For example, a probe may be a nucleic acid, polynucleotide or oligonucleotide whose sequence is sufficiently complementary to a target sequence in a cellular chromosome or other nucleic acid to hybridize to the latter structure under appropriate conditions. In various additional embodiments a probe may be an antibody or a portion thereof bearing a specificity determining binding site that specifically targets a cellular structure.

As used herein "representation" relates generally to any visual, graphical, numerical, or similar assembly of information that characterizes a result obtained using a particular detection method to examine a biological sample. By way of nonlimiting example, a representation includes an image of a microscopic field that includes at least a portion of a biological sample, an image further modified for example by computer driven means to convey information by attaching color values to particular features in a field, a graphical presentation characterizing particular features derived from an image of a sample, and a table of values or verbal entries characterizing features derived from an image.

As used herein "target", "targeted", "targeting" and similar words or phrases relate generally to a cellular structure to which a probe is specifically directed. A target is any structure or component that is a member of a specific binding pair constituted of the probe and the target. The probe and target have high specificity and affinity for binding to each other, and low specificity and low affinity for a probe, or for a target, respectively, not intended to be recognized. For a probe that includes a nucleic acid or at least a specific sequence of bases, a target is a complementary sequence found in chromosomal or nucleic acid components of a cell. For a probe that is an antibody or specific binding fragment thereof, a target may be an antigenic or hapten structure found in a cell. In this framework, a probe is a "targeting" moiety, and the target structure is "targeted" by the probe.

By "automated microscope" it is meant a microscope capable of receiving slides and automatically scanning and analyzing such slides by way of algorithms.

"Target" and "drug target" is also used herein to describe the drug's mechanism of action or how the drug causes it's effect in a human or animal. For example the target of an enzyme inhibitor is often the active site of an enzyme and competition with the substrate inhibits the catalytic conversion of substrate to product. A receptor antagonist targets the receptor and interferes with the endogenous ligand for that receptor. Similarly therapeutic antibodies of often target ligands by binding to the ligand to prevent engagement with the receptor.

By "robotic digital microscopy platform" it is meant as an automated microscope that automatically loads microscope slides, automatically scans the slides and digitally records images of material on the slide, and is operationally configured to detect one or more probes.

Also referred to herein are "markers", "biomarkers" and "surrogate". This entities are proven or proposed substitutes for clinical end points. For example we assert circulating tumor cells measurement by the embodiments of the invention herein are markers or surrogates clinical observations such as time to death.

"Characteristic features" or "features" refer to herein are used to mean chemical or physical properties that are targets for probes. This includes but is not limited antigens on the surface of a cancer cell or a particular sequence of DNA in the chromosome of a cell.

5. DETAILED DESCRIPTION OF EMBODIMENTS OF THE INVENTION

In one embodiment, an automated method of detecting circulating tumor cells in fluids obtained from patients, the tumor cells characterized by chemical and physical features of the cells, and generating information used to diagnose and/or monitor therapeutic progress comprising the steps of
 a) obtaining fluid from an individual;
 b) partially purifying tumor cells in fluid;
 c) contacting partially purified tumor cells with one or more distinguishable labeled probes directed to one or more characteristic features predetermined to identify tumor cells among normal cells feature under conditions to sufficiently affix labeled probe to withstand processing;
 d) analyzing said labeled cells with a high throughput robotic digital microscopy platform using
  (i) a low magnification to locate said labeled cell followed by,
  (ii) a high magnification for verification of cells bearing at least one said labeled probe; and from additional probes directed to characteristic features of the chromosome determine chromosomal integrity as an indication of malignant cell type.
 e) automatically reporting results of the analysis of step (d);
 wherein steps d-e are carried out without intervention by a human.

In another embodiment, there is disclosed an automated method of detecting and enumerating circulating tumor cells in fluids obtained from patients, said methods comprising the steps of:
 (i) obtaining a microscope slide having deposited thereon a cell population sample with one or more cancer cells therein, contacted with one or more distinguishable labeled probes directed to one or more characteristic features predetermined to identify tumor cells among normal cells, wherein said contacting is done under conditions sufficient to affix labeled probe;
 (ii) analyzing said labeled cells on a high-throughput robotic digital microscopy platform programmed to automatically:
  (a) locate said labeled cell at low magnification; followed by
  (b) verification of cells bearing at least one said labeled probe at high magnification;
  (c) determine a cell as a tumor cell if said labeled probe is detected at high magnification;
  (d) automatically counting normal cells and cancerous cells in a field; and
  (e) providing a representation of said cancerous cells in said normal cell count.

In yet determining embodiment, there is disclosed a method for detecting a whether circulating tumor cell is a prostate cancer cell, said method comprising the steps of:

(i) obtaining a slide carrying peripheral blood from a prostate cancer patient pre-, post, or during, treatment for prostate cancer, the peripheral blood being treated with distinguishable labeled probes directed to one or more characteristic features predetermined to identify tumor cells among normal cells; wherein said labeled probes comprise a first, second, third, fourth and fifth probes directed against a first, second, third, fourth and fifth characteristic feature of said tumor cell; wherein said first probe is a monoclonal antibody and said first characteristic feature is epithelial cell marker cytokeratin 7/8;

said second probe is a monoclonal antibody and said second characteristic feature is prostate specific antigen;

said third probe is a monoclonal antibody and the third characteristic feature is epithial adhesion molecule EpCam;

said fourth probe is a chromosome enumeration probe and said fourth characteristic feature is pericentromeric regions of chromosome 7 and 8;

said fifth probe is a chromosome enumeration probe said forth characteristic feature is pericentromeric regions of chromosome 17 and 18;

and wherein the peripheral blood if further stained with DAPI;

(ii) analyzing said slide on a high throughput robotic digital microscopy platform programmed to automatically:
  (a) locate cells bearing at least one of said first, second or third probes at low magnification; followed by
  (b) determine any binding of at least one of said fourth probe and said fifth probe at high magnification; and
(iii) automatically reporting malignant cells if cells are determined to bear at least one of said first, second, and third probes and at least one of said fourth or fifth probes.

In one such embodiment, the circulating tumor cell is a prostate cancer cell and the first probe is CAM5.2; the second probe is ER-PR8; the third probe is AUA1; the fourth probe is CEP7; and the fifth probe is CEP8.

Also disclosed is a method for detecting circulating tumor cells related to ovarian or colorectal cancer comprising the steps of:

(i) obtaining slide comprising peripheral blood from said ovarian or colorectal cancer patient pre-treatment, post-treatment or concurrent with treatment for said cancer contacted with distinguishable labeled probes directed to one or more characteristic features predetermined to identify tumor cells among normal cells; wherein said distinguishable labeled probes comprise a first, second, third, and fourth probes directed against a first, second, third, and fourth characteristic feature of said tumor cell; wherein said first probe is a monoclonal antibody and said first characteristic feature is epithelial cell marker cytokeratin 7/8;

said second probe is a monoclonal antibody and the second characteristic feature is epithial adhesion molecule EpCam;

said third probe is a chromosome enumeration probe and said third characteristic feature is pericentromeric regions of chromosome 7 and 8;

said forth probe is a chromosome enumeration probe said forth characteristic feature is pericentromeric regions of chromosome 17 and 18;

and wherein the peripheral blood is further stained with DAPI;

(ii) analyzing said slide on a high throughput robotic digital microscopy platform programmed to automatically:
  (a) locate cells bearing at least one of said first, and second probes at low magnification; followed by
  (b) determine any binding of at least one of said third probe and said fourth probe;
(iii) automatically reporting ovarian or colorectal malignant cells if the cells are determined to bear at least one of said first and second probes and at least one of said third and fourth probe.

In one embodiment, the fluid obtained from male patients is peripheral blood and intended for the detection of prostate cancer cells for the early detection of prostate cancer. The tumor cells are partially purified with the monocyte fraction by density gradient centrifugation or filtration and then labeled with a first antibody such as CAM5.2 directed to a first characteristic feature of a cancer cell such as the epithelial cell marker cytokeratin 7/8; and the second labeled probe is a second antibody such as ER-PR8 directed to second characteristic feature of a prostate cancer cell such as prostate specific antigen. In this embodiment, the cells are further contacted with a third and forth labeled probe wherein the probes are labeled sequences of nucleic acids complementary in sequence to third and forth characteristic feature of the cancer chromosome of prostate cancer cells predisposed to aberrant replication and resulting in a high incidence of polysomy. Such probes may comprise, for example, chromosome enumeration probes (CEP) designed to hybridize with pericentromeric regions of chromosome 7 and 8 and for chromosome 17 & 18 known for a high incidence of polysomy in prostate, colorectal and ovarian cancer. Finally cells are counter stained with a nuclear stain such as DAPI.

Further to this embodiment, automatic representation of the labeled features characteristics of the cancer cell is generated by an automatic microscope where distinguishable probes are enabled by use of distinguishable labels of distinct colors. Cancer cells are identified by automatic scanning cells containing the labeled characteristic feature of cancer cells. For example cells maybe scanned at low power (2×-15× (for example, 10×) to facilitate rapid of identification of cells that share both PSA and cytokeratin 7/8. These cells may be further automatically examined at high power, for example 100×, to count dots arising from labeled probes 3 & 4 to determine polysomy associated with chromosomes 7 & 8 and chromosomes 17 & 18. Finally combinations and permutations of the presence of probes 1, 2, 3, 4 and others such as AUA1 automatically acquired after appropriate training sets is used to designate as cancer cells. In this embodiment, a cell labeled with probes 1 & 2 and polysomic with respect to CEP 7 (probe 3) and CEP 8 (probe 4) is a circulating tumor cell designated a prostate cancer cell.

In another embodiment, the fluid obtained from female patients is peripheral blood for the detection of ovarian cancer cells for the early detection of ovarian cancer. The tumor cells are partially purified with the monocytes by density gradient centrifugation or filtration and then labeled with a first antibody such as CAM5.2 directed to a first characteristic feature of a cancer cell such as the epithelial cell marker cytokeratin 7/8; and the second labeled probe is a second antibody such as AUA1 directed to second characteristic feature of a cancer cell such as EpCam. At this point samples may or may not be counter stained with DAPI to highlight DNA. In this embodiment, the cells are further contacted with a third and forth labeled probe wherein the probes are labeled sequences of nucleic acids complementary in sequence to third and forth characteristic feature of the cancer chromosome of ovarian cancer cells predisposed to aberrant replication and resulting in a high incidence of polysomy. Such probes comprise chromosome enumeration probes (CEP) designed to hybridize with pericentromeric regions of chromosome 7 and 8 and for chromosome 17 & 18 known for a high incidence of polysomy in prostate, colorectal and ovarian cancer. At this point samples may or may not be counter stained with DAPI to highlight DNA.

Further to this embodiment, automatic representation of the labeled features characteristic of the cancer cell is generated by an automatic microscope wherein distinguishable probes are enabled by use of distinguishable labels of distinct colors. Cancer cells are identified by automatic scanning cells containing the labeled characteristic feature of cancer cells. For example cells maybe scanned at low power (10×) to facilitate rapid of identification of cells that share both EpCam and cytokeratin 7/8. These cells maybe further automatically examined at high power, for example 100×, to count dots associated with probes 3 & 4 within areas stained by DAPI to determine polysomy associated with chromosomes 7 & 8 and chromosomes 17 & 18. Finally combinations and permutations of the presence of probes 1, 2, 3, 4 and others automatically acquired after appropriate training sets is used to designate as cancer cells. In this embodiment, a cell labeled with probes 1 & 2 and polysomic with respect to CEP 7 (probe 3) and CEP 8 (probe 4) is designated an ovarian cancer cell.

The particular labels used in such methods may be automatically detected and processed by the automated microscope into a representation by means of software interfaced with the automated microscope. The software may be configured to cause automatic generation of the appropriate activating wavelengths or energies for the particular labels used, and automatic analysis based on the received input from the sample after or during the activation according to an expected response if a label is or is not present within a statistically acceptable range. The boundary software is further operatively configured to determine whether a cell is cancerous based upon a pre-determined algorithm of which labels are necessary for a positive cancer cell result. For example, the software may be designed to alter the wavelengths of impinging a slide by changing a bandpass to only certain wavelengths of light to impinge on the microscope slide sample, at different times, to determine whether an input received back from the sample during activations is indicative of the presence of a known label, and analyzing the detected label profile to determine, based on a pre-determined algorithm one or more cells are cancerous.

In another embodiment, the fluid is peripheral blood obtained from either female or male patients is peripheral blood for the detection of colorectal cancer cells for the early detection of colorectal cancer. This embodiment, other than the origin of blood, is identical to the previous embodiment. Cells derived from the peripheral blood of colorectal cancer patients with features that facilitate binding of the probes as above are designated colorectal cancer cells. Likewise, cells derived from the peripheral blood of colorectal cancer patients with features that facilitate binding of the probes as above are designated ovarian cancer cells.

In another embodiment in addition to immunostaining with AUA1/PSA and Cam5.2 followed by FISH probes for Chromosomes 7 & 8 or 17 & 18, antibodies to additional characteristic features of the circulating tumor cell or its environment. These characteristic features comprise prostate-specific membrane antigen, p53, MUC-1, the mismatch repair proteins hMLH1 and hMSH2, cell cycle specific proteins, cleaved caspase 3 for apoptosis, and phosphotyrosine residues on signaling proteins. In certain embodiments antibodies such as those and others listed are used without FISH.

In an embodiment, additional FISH probes are included for additional chromosomes that will be simultaneously used to help establish the tumorgenic phenotype. These FISH probes are directed against a group comprising HER2, EGFR and gene amplications.

In an another embodiment circulating cells are purified by filtration or affinity means using a semi-automated procedure to simultaneously purify multiple samples at once in computer controlled manner. The purified cells are then automatically applied to the microscope slide.

In another embodiment the method of detecting circulating cancer cells is used for the early detection of cancer. The presence of circulating cancer often long precedes the clinical manifestations of cancer. The method of this invention maybe used in an undirected screening mode or with the combinations of markers derived from higher through put methods and information from patient histories to screen a small group of patients predisposed to cancer prior to the rigorous identification by the present method.

Similarly in another embodiment the method maybe used to monitor reoccurrence or therapeutic progress. In this case the cancer is known thus allowing the specific design of probes for known characteristic features for that specific cancer or commonly occurring variants. Detection of cancer cells at a single point or a progressive increase in cancer cell number over a period of time enables the surgeon and/or oncologist to make informed decisions concerning continued or alternate therapy at a treatable stage in the disease. The presence of circulating cancer cell also allows the oncologist to select the pharmaceutical best suited for the particular cancer. For example by designing probes that identify mutations, amplifications or the resulting over-expressed receptors, enzymes ligands or other factors resulting in the disregulated growth. When the target is identified the pharmaceutical with the appropriate mechanism of action can be used. If for example the mutation and or over expression is the VEGF receptor the oncologist may select a directed therapeutic such as Avastin at an early stage in the cancer without exacerbating the disease by exposing the patients to a drug that will not work because the drug target is not present. In cases when no known therapeutic target is identifiable, the oncologist may choose an undirected nonspecific cytotoxic drug such a 5-fluorouridine at an earlier stage in the disease. It should be noted that the identified cancer cell feature responsible for the disregulated growth does not have to be identified directly. For example an over-expressed or constitutively active enzyme maybe identified by metabolically (same pathway) related enzymes or factors hyper- or hypo activated proteins proximal or distal to the over expressed target enzyme. For example a PI3K inhibitor maybe indicated by a mutated PTEN, the enzyme that hydrolyzes the PI3K product phosphatidylinositol phosphates. Alternately stated, the therapeutic target maybe identified by proteins or carbohydrates metabolically unrelated but co-stimulated by the therapeutic target.

Figure 4A:
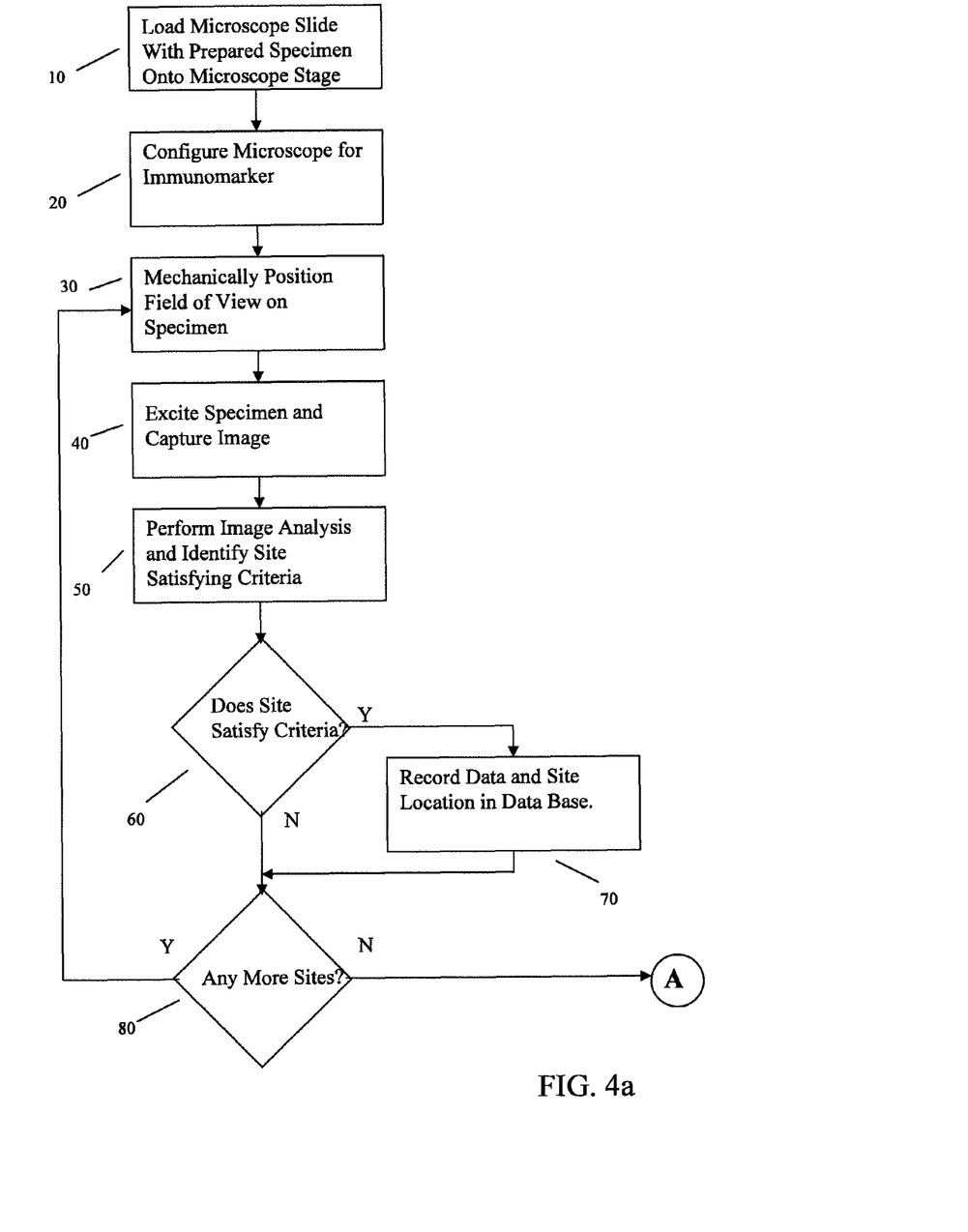
FIGS. 4a through 4c show a simplified flow chart of a software implementation of an exemplary embodiment of the present invention.
Figure 4B:
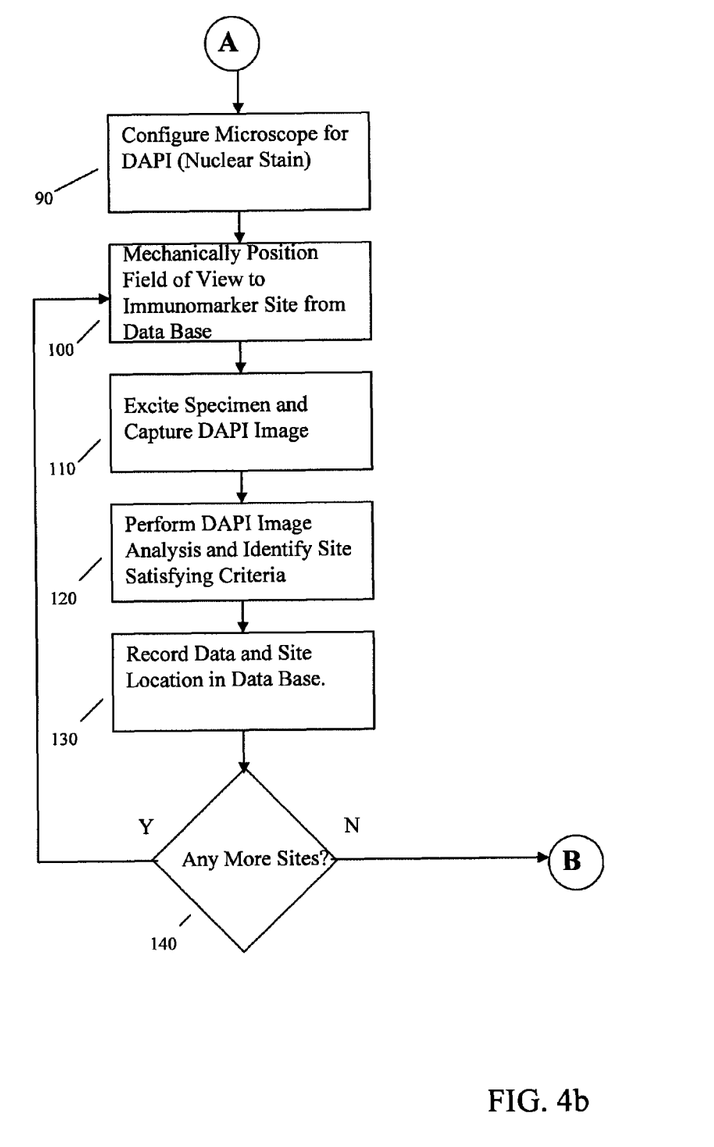
Figure 4C:
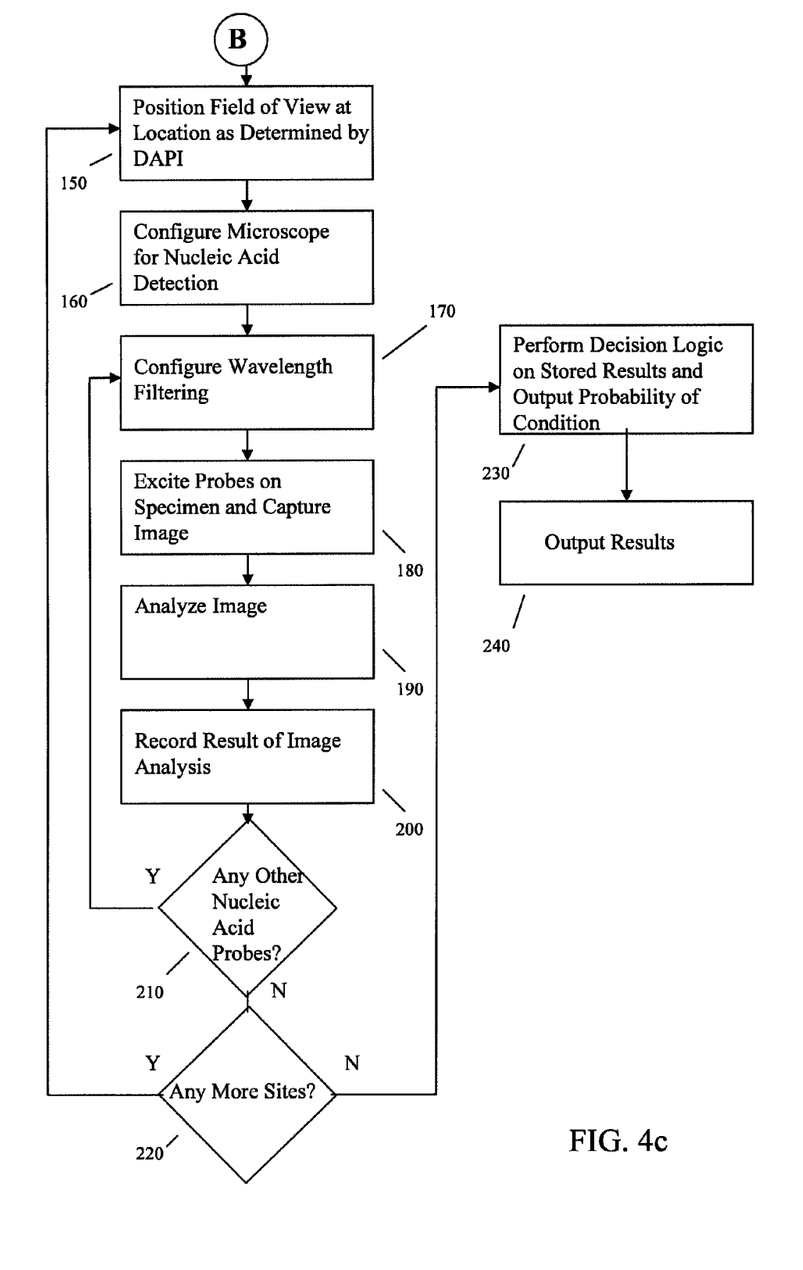

In an embodiment, the method may be implemented on an automated microscope. The specimen bearing slide is mounted onto the microscope stage. Turning to FIGS. 4a-4c, there is shown an simplified flow chart of a software implementation of an exemplary embodiment of the present invention. The automated microscope is configured (step 20) for immunomarker analysis at low magnification. The slide is positioned (step 30) to an initial field of view. The specimen is illuminated or excited as required by the probe and an image is captured (step 40). The capture image is subjected to computerized image analysis (step 50) to identify the presence of a candidate site for further investigation. If a candidate site is identified (step 60), its location and pertinent data are recorded (step 70) for further examination. If necessary (step 80), the microscope slide is repositioned to a next field of view, and the process is repeated. When all fields of view have been examined, the method proceeds to performing a chromosomal or DAPI analysis.

Having completed the immunomarker analysis, the microscope is reconfigured (step 90) to perform a DAPI analysis. This may include increasing the magnification, although in one advantageous embodiment low magnification is used. The slide is positioned (step 100) to a location which was determined by the immunomarker analysis. The specimen is illuminated as appropriate for DAPI and an image is captured (step 110). An analysis (step 120) is performed on the captured image and evaluated with respect to prescribed criteria. If the site satisfies the criteria, the location and pertinent data are recorded (step 130) for further evaluation. If there are additional candidate sites (step 140) identified during the immunomarker analysis, the specimen is repositioned and the process is repeated. If each of the identified sites has been examined, the method proceeds to nucleic acid detection analysis.

The slide is positioned (step 150) to image the first field of view as determined by the previous examinations, based for example on the location of the DAPI signal the Optionally DAPI Scan may be done at multiple magnifications. The microscope is configured (step 160) to perform nucleic acid detection analysis. This may include shifting to high magnification. The optical system wavelength filtering (step 170) is then configured as required by the first nucleic acid detection probe characteristics. The specimen is then illuminated and an image is captured (step 180). The captured image is subjected to automatic image processing which analyzes the image (step 190) and evaluates the results with respect to pre-established quantitative criteria. The location of the field of view and the image analysis results are recorded (step 200). If other nucleic acid detection probes are to be employed (step 210), the microscope is suitably reconfigured. If additional sites are to be examined (step 220), the specimen is appropriately repositioned, the wavelength filtering is reconfigured and the nucleic acid detection process is repeated. When all of the sites have been examined, the data collected throughout each step of the method is subjected to a automated decision logic (step 230) which computes the probability that one or more targeted conditions exist as determined from the specimen. The probability and other relevant data are output (step 240) in a report.

The inventors also see the detection of cancer cells by the method described reducing the cost of drug development and aiding patient health by preventing exposure of patients to anti-cancer drugs that are not designed for their particular cancer. Currently clinical trials are extremely expensive because of the lack of means to select patients likely to respond to the new drug. Alternatively said, methods are not available to effectively deselect patients where there is no chance of working. In an embodiment the invention herein, patients are selected for enrollment into clinical trials based on matching the characteristic features of their cancer cells with the mechanistic action of the new drug candidate. In an embodiment peripheral blood samples are taken and the monocyte fraction is isolated and treated with four or more labeled probes designed to identify the drug target. When the characteristic features of the cancer cell is appropriate with respect to the existing preclinical data concerning the mechanism of action, the patient is enrolled. In cases where the mechanism of action for the drug candidate is unknown, characteristic features of tumor cells are derived from training sets build from responders versus non-responders. Training sets consist of peripheral blood derived from patients known from a previous clinical trial to respond or not respond to the drug candidate. Characteristic features of the tumor cells derived from responders versus the non-responders are then analyzed by the instant invention to defined characteristic features that are unique to the responders. These features are then used as a selection criterion for enrollment of patients into subsequent trials. Determination of characteristic features of the tumor cells maybe coupled with high throughput assays methods for known biomarkers or protein, lipid or metabolite profiling methods to limit the number of features to be identified by the lower throughput method of the instant invention.

Following identification of characteristic features for patient enrollment, the instant inventions is used to monitor various surrogates of clinical response. Surrogates include the number of circulating cancer cells or the number of circulating cancer cells in combination with characteristic features identified by various probes. Clinical response and common clinical end points include time to death, time to progression and solid tumor size. The surrogate described may provide an earlier and more sensitive measure of the clinical response.

Additionally the described method of detecting circulating cancer cells is of great value to the development of new therapeutics.

In yet another embodiment, additional probes are included to further define patient populations by the presence or absence of additional characteristics regarding their circulating cancer cells. These additional characteristics define patient population predisposed to responding to a particular drug. In a related embodiment, a circulating tumor cell identified and precisely located on a slide is removed by known micromanipulators. Micromanipulators include laser dissection or laser capture means to permit profiling of proteins, carbohydrates, genes and lipids of the signal cell. This profiling permits identification of factors relevant to treatment unavailable in mixed cell population.

Early detection of a cancer is often critical for successful cancer treatment. Colorectal cancer patients who present with Duke's stage A at the time of diagnosis (11% of all cases) have excellent 5-year survival rates (83%), whereas for patients who present with Duke's stage D (29% of all cases), 5-year survival rates are 3% (26). Unfortunately, early detection, even with some of the currently proposed screening approaches, is not routinely possible with either colorectal or prostate cancer. Clinical data indicate that tumor cells may be shed into the blood many years before the presence of evident clinical symptoms. Thus, a significant number of colorectal cancer patients present with metastases at the time of diagnosis. The detection of circulating tumor cells could provide an easy, fast and non-invasive method for early detection of cancer. Patients with CTC could then be followed up with more invasive procedures, such as colonoscopy with a low probability of false positive diagnoses. The extent of false negatives will depend critically on the sensitivity of the assay. CTC should also be valuable for monitoring disease progression and response to treatment.

The unexpected result regarding the instant invention is the high sensitivity and specificity. This unexpected response relates the unique combination of automated immuno- and FISH-probes not achieved in separate manual procedures.

Figure 1A:
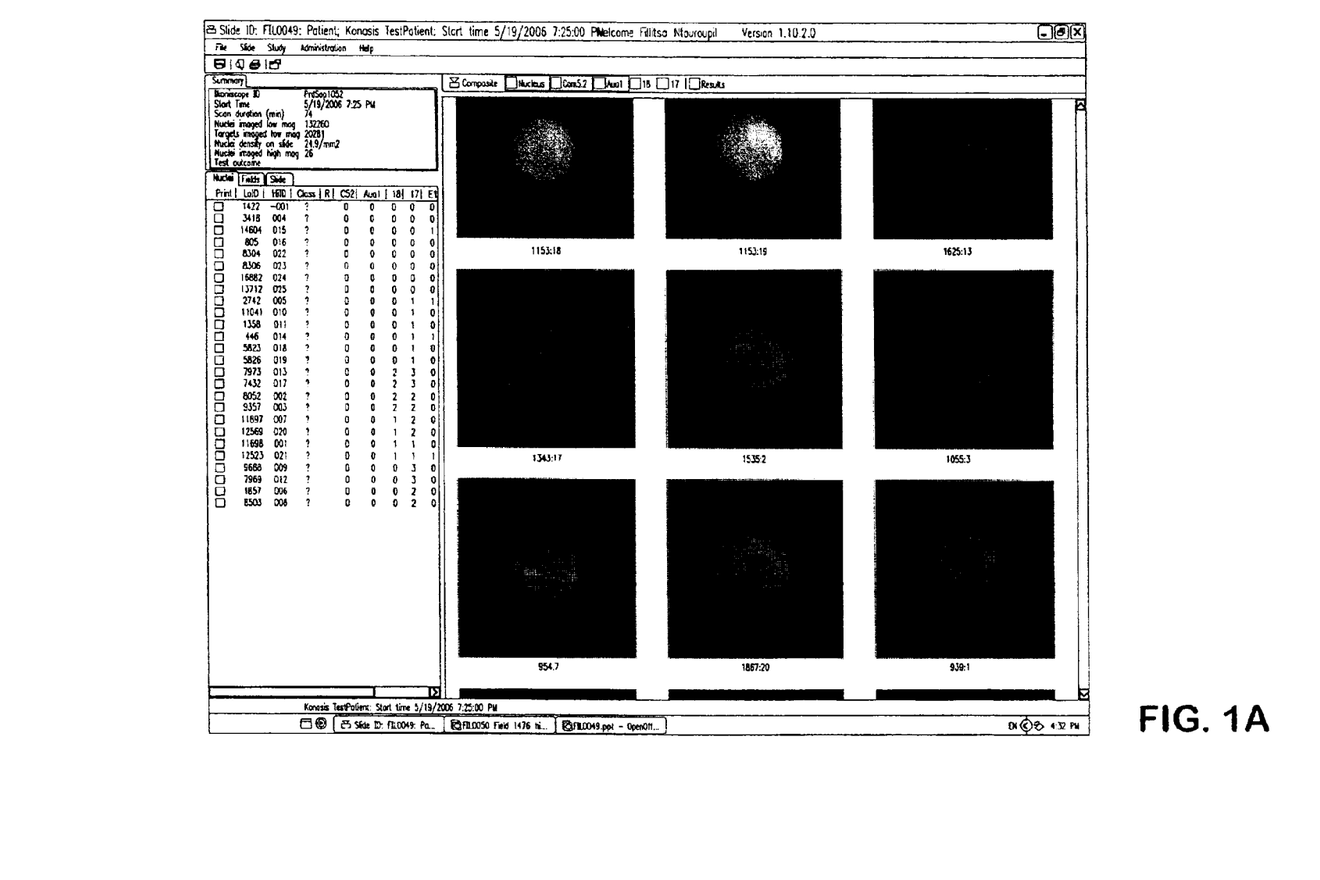
FIGS. 1A and 1B are scans of C32 cell spikes in normal donor blood after Lymphoprep™ isolation, immunostaining and FISH.
Figure 1B:
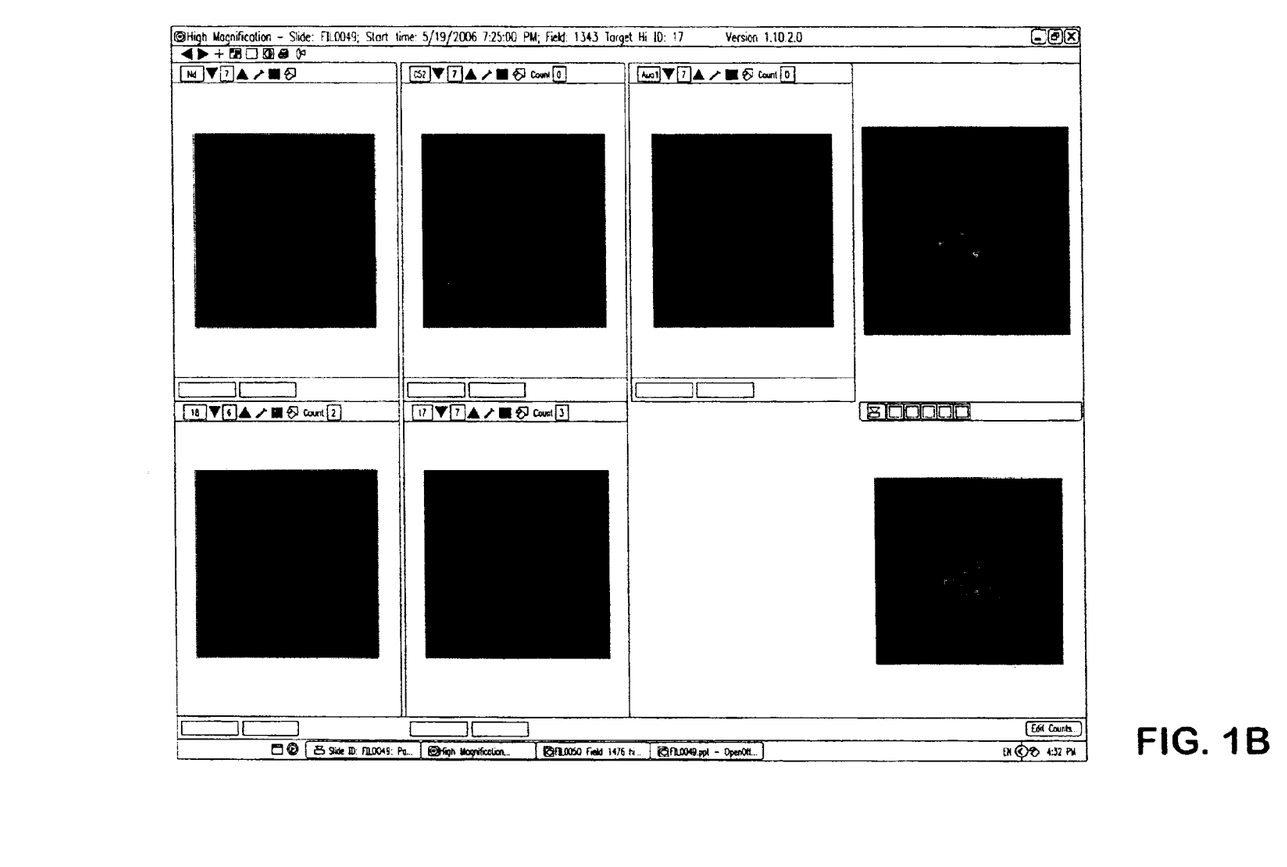

Cancer cells spiked into normal blood and isolated by either density gradient centrifugation or filtration is shown FIG. 1.

Table 3 compares cells from cancer patients with healthy patients. Of 25 colorectal patients circulating cancer cells were identified in 23 of the patients. Circulating cancer cells were identified in all prostate (10) and ovarian (4) patients whereas no circulating cancer cells were found in healthy controls. Furthermore the unusually high sensitivity, with detection limits at least 0.3 cells/ml, permits the use of small volumes of patient blood and the earliest detection of metastatic cancers. Of further value of this sensitivity is found in the comparison of PSA levels with the presence of circulating cancer cells. Of the 10 prostate cancer patients analyzed, the seven men who presented with elevated PSA levels but had no evidence of malignancy upon biopsy, CTCs were detected (1.4-1.7 cells/ml). This is an indication that these patients are at high risk and should be monitored. Detection of circulating tumor cells by the instant invention is a logical follow-up before moving to invasive surgical procedures. The high sensitivity and the specificity of the instant invention relating to the automated use of both immuno- and FISH probes. As indicated, this provides life saving value to an unmet medical need.

6. FURTHER EXEMPLARY EMBODIMENTS

Materials and Methods 6.1 Cell Lines

The colorectal carcinoma cell line C32 (36) and the prostate carcinoma cell line LNCaP (37) were cultured as previously described. Other cell lines were from the Cancer and Immunogenetics laboratory collection. Cell counts were determined by a Cellometer® automatic cell counter (Nexcelom Bioscience, Lawrence, Mass., USA) and 5-1000 cells were spiked into donor blood to estimate recovery yield. Alternatively, 1-3 cells were micropipetted into blood. All spiking experiments were performed in triplicate.

6.2 Blood Sample Preparation

Blood samples were obtained from 10 biopsy-proven prostate cancer patients, 25 colorectal cancer and 4 ovarian cancer patients. In addition, blood was collected from seven individuals with elevated serum prostate-specific antigen (PSA) levels but no evidence of malignancy upon biopsy. Blood samples were collected prior to, and within a few weeks of the pre-operative biopsy. The blood samples collected from patients 21-71 years old were used for spiking experiments and as normal controls. Informed consent was obtained from all patients and donors participating in this study. Investigations were performed after approval by the appropriate research ethical committee.

6.3 Isolation of Circulating Tumor Cells by Lymphoprep™

Lymphoprep™ (Ficoll-Isopaque or "Ficoll") was used for the isolation of mononuclear cells from the blood (Axis-Shield, Oslo, Norway). Mononuclear cells (monocytes and lymphocytes) have a lower buoyant density than the erythrocytes and the granulocytes. The vast majority of mononuclear cells have densities below 1.077 g/ml. These cells can therefore be isolated by centrifugation on an iso-osmotic medium with a density close to 1.077 g/ml, which allows the erythrocytes and the granulocytes to sediment through the medium while retaining the mononuclear cells at the sample/medium interface.

Blood was collected into tubes containing Acid Citrate Dextrose (ACD) as anticoagulant and diluted by addition of 2 volumes of RPMI medium. 6 ml of the diluted blood were carefully layered over 3 ml of Lymphoprep™ in a 15 mm centrifuge tube and centrifuged at 800×g for 20 minutes at room temperature (RT) in a swing-out rotor. After centrifugation the mononuclear cells form a distinct band at the sample/medium interface. The cells were removed from the interface using a Pasteur pipette without removing the upper layer. The harvested fraction was diluted with at least 3 volumes of RPMI to reduce the density of the solution and the cells were pelleted by centrifugation for 10 minutes at 250×g. The cell pellet was resuspended in 10 ml PBS (phosphate buffer saline, pH 7.4) and centrifuged again. The cells were resuspended in 5 ml PBS. The cell suspension was further diluted with PBS to yield a concentration of approximately 270000 cells/ml. The cell suspension was deposited on poly-L-lysine coated, single well chamber slides (IkoniSlide, Ikonisys Inc, New Haven, Conn.), using 3 ml of the cell suspension (approximately 800000 cells) per slide, in order to have the optimum density of deposited cells. The cells were left to settle at room temperature for 30 min and they were then fixed with ice-cold methanol for 5 min followed by 2% formaldehyde in PBS for 5 min. The slides were washed with PBS (2×5 min) followed by a 5 min wash with PBS-T (0.05% Tween-20 in PBS).

6.4 Isolation of Circulating Tumor Cells by Filtration with Track-Etched Membranes Blood was collected into tubes containing anticoagulant (ACD), diluted by addition of 10 volumes of PBS containing 0.2% formaldehyde, 0.037% EDTA and 0.1% BSA and incubated at room temperature for 15 min. A Nucleopore (Whatman) track-etched polycarbonate membrane filter (8.0 um pore size, 25 mm diameter) was placed shiny side up in a reusable syringe filter holder (PALL Life Sciences, Ann Arbor, Mich., USA) and a syringe barrel was used as a funnel. The use of a vacuum manifold (VM20; sigma, St Louis, Mo., USA) allows processing of 20 samples simultaneously. Suction was applied by a vacuum pump briefly at the beginning of the filtration and then the sample was allowed to flow through by gravity. The vacuum produced by the Misrosart® maxi vac pump (Sartorius, Goettingen, Germany The diluted blood was filtered through the Nucleopore membrane and washed with 100 ml PBS. The cells retained on the filter were fixed with ice-cold methanol for 5 min followed by 2% formaldehyde in PBS for 5 min. After washing with 100 ml PBS, the filter was removed from the filter holder and processed for antibody staining as described below. This procedure for fast and efficient isolation of epithelial cells with minimum manipulation, thereby maintaining cellular integrity.

6.5 Antibody Staining

All incubations were performed at room temperature, in humidified chambers, protected from light. The cells were first incubated for 30 min in a blocking solution containing 0.01 g/ml blocking reagent in PBS-T (Tyramide Signal Amplification Kit™, Molecular Probes Inc.), followed by 30 min incubation with 2 µg/ml AUA1 in blocking solution. AUA1 is a mouse anti-EpCam monoclonal antibody.

Alternatively, in the case of some of the prostate cancer patients, a mouse monoclonal antibody against the prostate specific antigen (PSA) was used, at a concentration of 10 µg/ml in blocking solution (Abcam: ER-PR8). Specific binding was detected using HRP-conjugated Goat anti-mouse antibody (5 µg/ml in blocking solution, 30 min) followed by green-fluorescent Alexa Fluor 488 tramide labeling according to the manufacturer's protocol (TSA; Molecular Probes Inc.). Peroxidase activity was quenched by incubating for 30 min with 2% H2O2 in PBS-T, the cells were incubated for 30 min with 7 ug/ml of the biotinyylated muse monoclonal antibody Cam 5.2 against cytokeratins 7/8 (Makin et al 1984). Specific binding was detected using HRP-conjugated streptavidin (5 ug/ml in blocking solution, 30 min) followed by labelling with far-red fluorescent Alexa Fluor 647 tyramide (which is spectrally similar to Cy5). Specimens were cover slipped with Vectashield mounting medium (Vector, Burlingame. Calif., USA) containing DAPI (4'; 6' diamidino-2-phenylindole), to, preserve fluorescence and counter stain the DNA. The use of the Tvramide signal amplification detection method (Molecular probes Inc.) enables the combination of immunostaining with FISH, without substantial loss of the antibody fluorescence signal intensity. The fluorescent dye-labeled tyramide derivatives are activated by the HRP conjugated to the secondary antibody and are covalently coupled to nucleophilic residues in the vicinity of the HRP-target interaction site. The tyramide signal amplification results in increased sensitivity of detection and stronger signals. In addition, the covalent nature of the binding of fluorescent dyes to targets through tyramide renders the signals more stable and resistant to the conditions the specimens are subjected to during FISH.

6.6 Fluorescence in situ Hybridization

Slides with positively immunolabelled cells on them were dehydrated in ethanol series (50,75 and 100% ethanol, 30 s each), air-dried at 37° C. for 15 min and subsequently incubated at 37° C. for 3 min in a pre-warmed solution containing 0.001% pepsin and 10 mM HCl. After washing with 50 mM $MgCl_2$ in PBS for 5 min, cells were fixed for 10 min at RT with a solution of 2% formaldehyde and 50 m~ MgClz in PBS. After washing in PBS (2×5 min, RT) and 2×SSC (Ismin, 37"C), the slides were dehydrated in ethanol series and air-dried. Chromosome enumeration probes (CEP) for chromosomes 7 (aqua), 8 (aqua), 17 (orange) and 18 (aqua) were mixed with hybridization buffer, and denaturation and hybridization were performed according to the manufacturer's instructions (Vysis, Downers Grove, Ill., USA). Following overnight hybridisation, the slides were washed in pre-warmed 0 4× SSC buffer with 0 3% NP-40 for 3 min at 72OC followed by 2 min in 2× SSC with 0 1% NP-40 and 5 min in 2×SSC. After air-drying for 2 min, the specimens were coverslipped with DAPI-containing Vectashield mounting medium.

6.7 Robotic Fluorescence Microscopy

Identification and quantification of immunolabelled cells and FISHanalysis were performed using the Ikoniscope© imaging system (Kilpatrick et al, 2004; Evans et al, 2006; Ntouroupi et al, 2007). The Ikoniscope robotic, high-throughput, image acquisition and display microscopy system, is developed by Ikonisys for rare cell identification and analysis. It uses epifluorescence optics manufactured by Olympus (Tokyo, Japan). Slides are fed to the instrument through an automated slide/cassette feeder that provides unattended handling of 175 slides. The microscope stage is built for high speed and accuracy of slide movement in each of the x, y and z directions. Image capture is performed through a high-resolution and high-sensitivity monochrome charge-coupled device camera (Hamamatsu Orca ER; Hamamatsu Photonic Systems, Bridgewater, N.J., USA). Carefully controlled exposure setting and automated focusing, combined with three-dimensional image acquisition, are essential for rare cell detection. Cell identification takes place in real. time, using image analysis for the detection and quantification of antibody and FISH signals. Preparations are first scanned at low magnification (×10) to identify cells carrying both immunolabelled markers. Selected target cells are then revisited at high magnification (×100) for verification and enumeration of FISH signals. Results are displayed using the IkoniLAN© viewer software that allows evaluation of low-magnification images from all scanned fields as well as highmagnification images of target cells in all fluorescence channels. All stored information, raw images, processed images and processing results are made available to the reviewers through the IkoniLAN server both in local area computer networks as well as wide area networks using the internet.

6.8 Model Systems Used to Develop the Procedure

Blood samples collected from healthy donors were 'spiked' with a known number of cells of colorectal (C32) or prostate (LNCaP) carcinoma derived cell lines. The 'spiked' model systems were processed through the isolation and antibody detection protocol as described above.

6.9 Sensitivity Tests Using Model Systems

Initial assay development was carried out using Lymphoprep processing of normal blood samples spiked with known numbers of cells from the CRC line C32 and other cell lines. Examples of imaged cells from a spiking experiment are shown in FIG. 1. Mononuclear cells were deposited on slides, immunostained with antibodies against EpCam (AUA1) and cytokeratins 718 (Cam5.2), and FISH carried out for the enumeration of chromosomes 17 and 18, as described in Materials and Methods. Chromosomes 17 and 18 were chosen because C32 cells exhibit trisomy for 17 and are diploid for 18 and therefore can be used to test the specificity of detection by FISH. Between 90 and 100% of cells deposited on slides were detected down to a dilution of one C32 cell micropipetted into 8 ml of blood and similar results were obtained using the LNCaP prostate carcinoma cells. FIG. 1 shows screen captures of the Viewer software that displays the data produced by the Ikoniscope scanning system. (Kilpatrick et al, 2004; Evans et al, 2006). FIG. 1A shows a high magnification (×100) target gallery screen displaying images of identified C32 cells. The displayed images are composites of the Cy5Ired (AUA1), green (Cam5.2) and DAPI (blue) channels. FIG. 1B displays one of the target C32 cells at high magnification (×100). The three dots corresponding to chromosomes 17 appear in yellow and the two dots corresponding to chromosomes 18 appear in aqua, which fits in with the-known-karyotype of C32 cell;—7.2 Measurements of circulating cancer cells in patient peripheral blood purified by density gradient centrifugation and filtration.

Figure 2A:
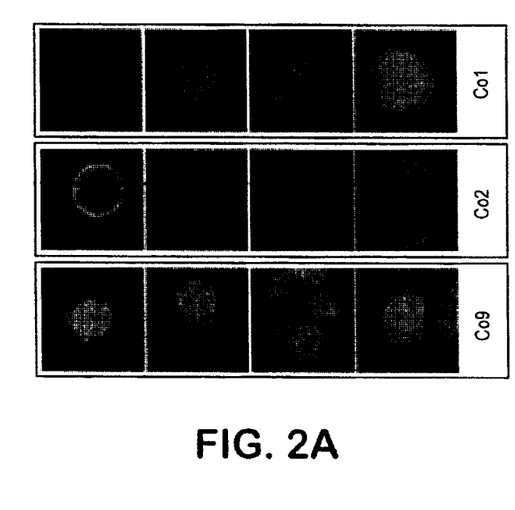
FIGS. 2A and B are scans of circulating tumor cells from the blood of colorectal and prostate cancer patients after Lymphoprep™ isolation, immunostaining and FISH.
Figure 2B:
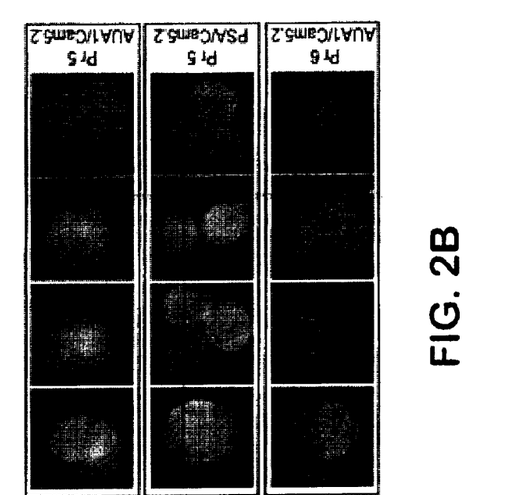

Representative cells identified in blood samples from colorectal and prostate cancer patients, using Lymphoprep isolation and antibody labelling; are shown in FIG. 2. These demonstrate the presence of very clearly identifiable doubly labelled epithelial, and so presumptive tumour, cells in both sets of patients.

Figure 3A:
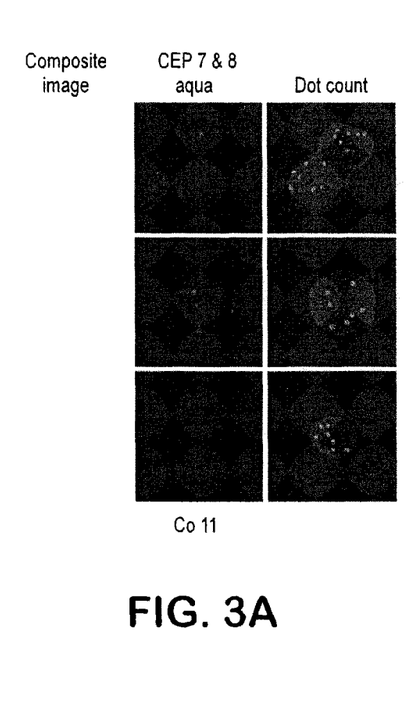
FIGS. 3A and 3B are scans of circulating tumor cells from the blood of colorectal and ovarian cancer patients after isolation by filtration, immunostaining and FISH.
Figure 3B:
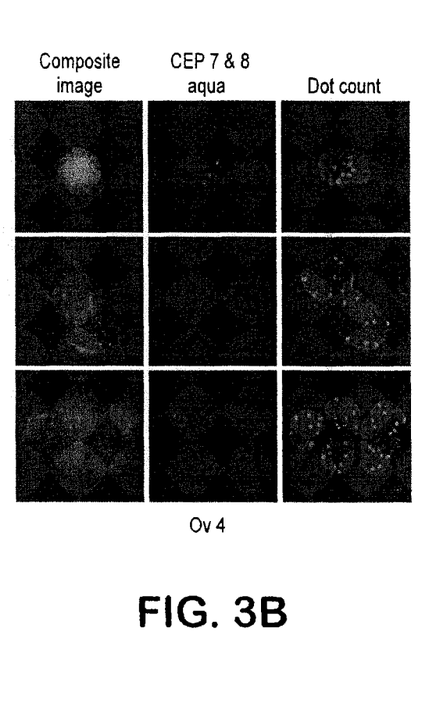

Spiking reconstruction experiments using the much simpler and more rapid filter procedure, with a range of cell concentrations and 10 different cell lines, gave recoveries of 94-100% (data not shown). This is consistent with measurements of the mean diameters of cells from 20 different cancer cell lines, showing that, on average, more than 90% cells had a mean diameter greater than 8 um, which is the filter pore diameter (data not shown). Representative cells identified from a colorectal and an ovarian cancer patient as reacting with both the EpCam and cytokeratin 7/8 antibodies, and analysed by FISH for the enumeration of chromosomes 7 and 8 are shown in FIG. 3. Each cell is clearly identified by reaction with both antibodies and has a definitely abnormal chromosome count: seven dots for the colorectal and eight dots for the ovarian cancer, compared with the four dots expected. These cells are thus unequivocally identified as CTCs with a readily recognizable morphology. The choice of these particular chromosomes was based on a database search, which showed high incidence of polysomies for chromosomes 7 and 8 in colorectal, prostate and ovarian cancer cell lines and patient cases (http:llwww.cgap.nci.nih.gov/Chromosomes/Mitelman, http://www.ncbi.nlrn.nih.gov/sky/skyweb.cgi).

No cells reacting with both antibodies to EpCam and cytokeratins 7/8 have been found in any of the four (two females, two males) Lymphoprep and seven (three females and four males) filter-prepared healthy control samples (Table 1 and 2).

TABLE 1

Circulating tumor cells isolated with Lymphoprep ™ from blood samples of colorectal and prostate cancer patients and normal donors.

Colorectal Cancer

| Isolation method | Co No. | Tumor Stage | Nodal Stage | Metastasis | Cells/ml of blood | Blood analyzed (ml) | Cells detected |
|---|---|---|---|---|---|---|---|
| LYMPHOPREP | ♂1 | T3 | N0 | M0 | 1.5 | 8.8 | 13 |
| | ♂2 | T4 | N0 | M0 | 9.3 | 5.8 | 54 |
| | ♀3 | T3 | N0 | Mx | 1.2 | 4.1 | 5 |
| | ♂4 | T3 | N1 | M0 | 0.1 | 7.7 | 1 |
| | ♀5 | T3 | N0 | M0 | 0.6 | 1.5 | 1 |
| | ♂6 | T3 | N2 | M1 | 0 | 8.2 | 0 |
| | ♂7 | T3 | N1 | M1 | 0.3 | 6.55 | 2 |
| | ♂8 | T3 | N2 | M0 | 0.5 | 6.53 | 3 |

Prostate Cancer

| Isolation method | Prost. No. | PSA | Gleason score | Cells/ml of blood | Blood analyzed (ML) | Cells detected |
|---|---|---|---|---|---|---|
| LYMPHOPREP | 1 | 95.4 | 8 | 9.4 | 6.4 | 60 |
| | 2 | 6.1 | 6 | 2.2 | 7.3 | 16 |
| | 3 | 23.6 | 7 | 3.5 | 4.9 | 17 |

NORMAL CONTROLS

| Isolation method | No. | Cell/ml blood | Blood analyzed (ml) | Cells detected |
|---|---|---|---|---|
| LYMPHOPREP | ♀1 | 0 | 8 | 0 |
| | ♀2 | 0 | 8 | 0 |
| | ♂3 | 0 | 8 | 0 |
| | ♂3 | 0 | 8 | 0 |

Elevated PSA/Benign biopsy

| Isolation method | No. | PSA | Cells/ml of blood | Blood analyzed (ml) | Cells detected |
|---|---|---|---|---|---|
| LYMPHOPREP | 1 | 5.7 | 0 | 8 | 0 |
| | 2 | 7.5 | 0 | 7.5 | 0 |

Cells from colorectal patients were immunostained with AUA1 and Cam 5.2 followed by enumeration of chromosomes 7 and 8 by FISH. For prostate cancer patients, treatment was the same but with Cam 5.2 and AUA1 or antibodies to PSA.

TABLE 2

Circulating tumor cells isolated by filtration from peripheral blood samples of colorectal and ovarian cancer patients and from healthy donors.

Colorectal Cancer

| Isolation method | Co No. | Tumor Stage | Nodal Stage | Metastasis | Cells/ml of blood | Blood analyzed (ml) | Cells detected |
|---|---|---|---|---|---|---|---|
| FILTER | ♂11 | T4 | N1 | M0 | 10.2 | 5.5 | 56 |
| | ♂12 | T3 | Nx | M0 | 5.9 | 7.5 | 44 |
| | ♂13 | T3 | N2 | M0 | 0.9 | 8 | 7 |
| | ♂14 | T3 | N2 | M0 | 0.2 | 8.5 | 2 |
| | ♂15 | T2 | N0 | M0 | 2 | 7 | 14 |
| | ♂16 | T4 | N1 | M0 | 1.3 | 8.5 | 11 |
| | ♂17 | T4 | N2 | M0 | 0.7 | 7.5 | 5 |
| | ♂18 | T3 | N0 | M0 | 2.3 | 7 | 16 |
| | ♂19 | T3 | N0 | M0 | 2.9 | 8 | 23 |
| | ♂20 | T3 | N0 | M0 | 1.3 | 7.5 | 10 |
| | ♀21 | T2 | N1 | Mx | 0.3 | 8 | 2 |
| | ♀22 | T2 | N0 | Mx | 0.9 | 8 | 7 |
| | ♂23 | T3 | N0 | M0 | 3.9 | 8 | 31 |

TABLE 2-continued

Circulating tumor cells isolated by filtration from peripheral blood samples of colorectal and ovarian cancer patients and from healthy donors.

| | ♂24 | T3 | N1 | M0 | 0.5 | 8 | 4 |
|---|---|---|---|---|---|---|---|
| | ♂25 | T3 | N0 | M0 | 0 | 6.5 | 0 |

Prostate Cancer

| Isolation method | Prost. No. | PSA | Gleason score | Cells/ml of blood | Blood analyzed (ML) | Cells detected |
|---|---|---|---|---|---|---|
| FILTER | 4 | 40 | 9 | 0.3 | 7 | 2 |
| | 5 | 10.7 | 6 | 7.6 | 7 | 53 |
| | 6 | 11.2 | 6 | 5.9 | 7.5 | 44 |
| | 7 | 24.4 | 8 | 0.3 | 7 | 2 |
| | 8 | 6.1 | 6 | 0.7 | 7 | 5 |
| | 9 | 5.8 | 6 | 6.3 | 8 | 50 |
| | 10 | 25.9 | 8 | 3.7 | 7.8 | 29 |

NORMAL CONTROLS

| Isolation method | No. | Cell/ml blood | Blood analyzed (ml) | Cells detected |
|---|---|---|---|---|
| FILTER | ♀1 | 0 | 8 | 0 |
| | ♀2 | 0 | 8 | 0 |
| | ♂3 | 0 | 8 | 0 |
| | ♂3 | 0 | 8 | 0 |

Elevated PSA/Benign biopsy

| Isolation method | No. | PSA | Cells/ml of blood | Blood analyzed (ml) | Cells detected |
|---|---|---|---|---|---|
| FILTER | 3 | 9.3 | 0 | 8 | 0 |
| | 4 | 7.8 | 1.4 | 7 | 10 |
| | 5 | 7.2 | 1.7 | 7.5 | 13 |
| | 6 | 7.5 | 1.4 | 5.5 | 8 |
| | 7 | 9.3 | 0 | 8 | 0 |

NORMAL CONTROLS

| Isolation method | No. | Cells/ml of blood | Blood analyzed (ml) | Cells detected |
|---|---|---|---|---|
| FILTER | ♀5 | 0 | 8 | 0 |
| | ♀6 | 0 | 8 | 0 |
| | ♀7 | 0 | 8 | 0 |
| | ♀8 | 0 | 8 | 0 |
| | ♂9 | 0 | 8 | 0 |
| | ♂10 | 0 | 8 | 0 |
| | ♂11 | 0 | 8 | 0 |

Treatment is the same as in Table 2.

A summary of data obtained so far on 25 colorectal, 10 prostate and 4 ovarian cancer patients is shown in Table 3. Presumptive CTCs were not detected in only 2 out of 25 CRC patients, 1 of whom had no nodal involvement. The mean number of CTCs per milliliter was slightly lower (1.6) for the Lymphoprep than for the fiter-isolated (2.2) samples.

TABLE 3

Summary of results for CTC detection in all sample groups

| | | CTC Positive | Cells per ml blood | | |
|---|---|---|---|---|---|
| Sample Group | n | n (%) | Range | Mean | Median |
| Colorectal | 25 | 23 (92) | 0-10.2 | 1.96 | 0.9 |
| Prostate | 10 | 10 (100) | 0.3-9.4 | 3.99 | 3.6 |
| Ovarian | 4 | 4 (100) | 0.5-1.9 | 0.98 | 0.75 |
| Elevated PSA/NEM | 7 | 3 (42.9) | 0-1.7 | 0.64 | 0 |
| Healthy controls | 11 | 0 (0) | 0 | 0 | |

Abbreviations: PSA = prostate specific antigen; NEM = no evidence of malignancy upon biopsy In all 10 prostate cancer patients analysed, CTCs were detected. Among the seven men who presented with elevated PSA levels but had no evidence of malignancy upon biopsy, four had no detectable CTCs. In the remaining three cases, where the biopsy indicated no malignancy, CTCs were detected (1.4-1.7 cells/ml) strongly suggesting that these patients should be reinvestigated, or at least carefully followed up. It should be noted that in all three of the above-mentioned cases, the identified cells were positive for PSA as well as for AUA1 and Cam5.2. These data, although clearly very preliminary, suggest that the Ikoniscope based CTC detection may be an effective way to reduce the number of false-positives for prostate malignancy based on elevated PSA levels. All four ovarian cancer patients had presumptive CTCs. Table 2 presents the results by patient1control group, indicating the percentage of positive samples as well as the range, mean and median number of CTCs detected per milliliter of blood. Five patients (three CRCs, two ovarian) were analyzed by FISH for chromosomes 7 and 8 combined (see FIG. 3) and all had significantly more than four dots per cell.

While the invention has been described with respect to preferred embodiments, those skilled in the art will readily appreciate that various changes and/or modifications can be made to the invention without departing from the spirit or scope of the invention as defined by the appended claims. All documents cited herein are incorporated by reference herein where appropriate for teachings of additional or alternative details, features and/or technical background.

REFERENCES

1. Wong, S. Y. & Hynes, R. O. (2006) *Cell Cycle* 5, 812-7.
2. Deisboeck, T. S., Mansury, Y., Guiot, C., Degiorgis, P. G. & Delsanto, P. P. (2005) *Med Hypotheses* 65, 785-90.
3. Michaelson, J. S., Cheongsiatmoy, J. A., Dewey, F., Silverstein, M. J., Sgroi, D., Smith, B. & Tanabe, K. K. (2005) *Br J Cancer* 93, 1244-9.
4. Molnar, B., Sipos, F., Galamb, O. & Tulassay, Z. (2003) *Dig Dis* 21, 320-5.
5. Schuster, R., Max, N., Mann, B., Heufelder, K., Thilo, F., Grone, J., Rokos, F., Buhr, H. J., Thiel, E. & Keilholz, U. (2004) *Int J Cancer* 108, 219-27.
6. Tsavellas, G., Huang, A., McCullough, T., Patel, H., Araia, R. & Allen-Mersh, T. G. (2002) *Clin Exp Metastasis* 19, 495-502.
7. Pelkey, T. J., Frierson, H. F., Jr. & Bruns, D. E. (1996) *Clin Chem* 42, 1369-81.
8. Hamdy, F. C., Lawry, J., Anderson, J. B., Parsons, M. A., Rees, R. C. & Williams, J. L. (1992) *Br J Urol* 69, 392-6.
9. Li, G., Passebosc-Faure, K., Gentil-Perret, A., Lambert, C., Genin, C. & Tostain, J. (2005) *Anticancer Res* 25, 377-81.
10. Pinzani, P., Salvadori, B., Simi, L., Bianchi, S., Distante, V., Cataliotti, L., Pazzagli, M. & Orlando, C. (2006) *Hum Pathol* 37, 711-8.
11. Tong, X., Yang, L., Lang, J. C., Zborowski, M. & Chalmers, J. J. (2007) *Cytometry B Clin Cytom.*
12. Hu, X. C., Wang, Y., Shi, D. R., Loo, T. Y. & Chow, L. W. (2003) *Oncology* 64, 160-5.
13. Witzig, T. E., Bossy, B., Kimlinger, T., Roche, P. C., Ingle, J. N., Grant, C., Donohue, J., Suman, V. J., Harrington, D., Torre-Bueno, J. & Bauer, K. D. (2002) *Clin Cancer Res* 8, 1085-91.
14. Kowalewska, M., Chechlinska, M., Markowicz, S., Kober, P. & Nowak, R. (2006) *Eur. J. Cancer.*
15. Cama, C., Olsson, C. A., Buttyan, R., de Vries, G. M., Wise, G. J. & Katz, A. E. (1997) *J Urol* 157, 1748-51.
16. Altaras, M. M., Klein, A., Zemer, R., Zimlichman, S., Bernheim, J. & Fishman, A. (2002) *Gynecol Oncol* 86, 330-6.
17. Lukyanchuk, V. V., Friess, H., Kleeff, J., Osinsky, S. P., Ayuni, E., Candinas, D. & Roggo, A. (2003) *Anticancer Res* 23, 2711-6.
18. Cohen, S. J., Alpaugh, R. K., Gross, S., O'Hara, S. M., Smirnov, D. A., Terstappen, L. W., Allard, W. J., Bilbee, M., Cheng, J. D., Hoffman, J. P., Lewis, N. L., Pellegrino, A., Rogatko, A., Sigurdson, E., Wang, H., Watson, J. C., Weiner, L. M. & Meropol, N. J. (2006) *Clin Colorectal Cancer* 6, 125-32.
19. Rao, C. G., Chianese, D., Doyle, G. V., Miller, M. C., Russell, T., Sanders, R. A., Jr. & Terstappen, L. W. (2005) *Int J Oncol* 27, 49-57.
20. Yie, S. M., Luo, B., Ye, N.Y., Xie, K. & Ye, S. R. (2006) *Clin Exp Metastasis* 23, 279-89.
21. Koyanagi, K., O'Day, S. J., Gonzalez, R., Lewis, K., Robinson, W. A., Amatruda, T. T., Kuo, C., Wang, H. J., Milford, R., Morton, D. L. & Hoon, D. S. (2006) *Clin Cancer Res* 12, 1137-43.
22. Smerage, J. B. & Hayes, D. F. (2006) *Br. J. Cancer* 94, 8-12.
23. Morgan, T. M., Lange, P. H. & Vessella, R. L. (2007) *Front Biosci* 12, 3000-9.
24. Kilpatrick, M. W., Tafas, T., Evans, M. I., Jackson, L. G., Antsaklis, A., Brambati, B. & Tsipouras, P. (2004) *Am J Obstet Gynecol* 190, 1571-8; discussion 1578-81.
25. Evans, M. I., Sharp, M., Tepperberg, J., Kilpatrick, M. W., Tsipouras, P. & Tafas, T. (2006) *Fetal Diagn Ther* 21, 523-7.
26. Campbell, N.C., Elliott, A. M., Sharp, L., Ritchie, L. D., Cassidy, J. & Little, J. (2001) *Br J Cancer* 84, 910-4.
27. Racila, E., Euhus, D., Weiss, A. J., Rao, C., McConnell, J., Terstappen, L. W. & Uhr, J. W. (1998) *Proc Natl Acad Sci USA* 95, 4589-94.
28. Ried, T., Heselmeyer-Haddad, K., Blegen, H., Schrock, E. & Auer, G. (1999) *Genes Chromosomes Cancer* 25, 195-204.
29. Shackney, S. E. & Shankey, T. V. (1997) *Cytometry* 29, 1-27.
30. Katsura, K., Sugihara, H., Nakai, S. & Fujita, S. (1996) *Cancer Genet Cytogenet* 90, 146-53.
31. Bardi, G., Sukhikh, T., Pandis, N., Fenger, C., Kronborg, O. & Heim, S. (1995) *Genes Chromosomes Cancer* 12, 97-109.
32. Teixeira, M. R., Waehre, H., Lothe, R. A., Stenwig, A. E., Pandis, N., Giercksky, K. E. & Heim, S. (2000) *Genes Chromosomes Cancer* 28, 211-9.
33. Verdorfer, I., Hobisch, A., Culig, Z., Hittmair, A., Bartsch, G., Erdel, M., Duba, H. C. & Utermann, G. (2001) *Int J Oncol* 19, 1263-70.
34. Deger, R. B., Faruqi, S. A. & Noumoff, J. S. (1997) *Cancer Genet Cytogenet* 96, 166-73.
35. Fehm, T., Sagalowsky, A., Clifford, E., Beitsch, P., Saboorian, H., Euhus, D., Meng, S., Morrison, L., Tucker, T., Lane, N., Ghadimi, B. M., Heselmeyer-Haddad, K., Ried, T., Rao, C. & Uhr, J. (2002) *Clin Cancer Res* 8, 2073-84.
36. Browning, M. J., Krausa, P., Rowan, A., Bicknell, D.C., Bodmer, J. G. & Bodmer, W. F. (1993) *Proc Natl Acad Sci USA* 90, 2842-5.
37. Horoszewicz, J. S., Leong, S. S., Kawinski, E., Karr, J. P., Rosenthal, H., Chu, T. M., Mirand, E. A. & Murphy, G. P. (1983) *Cancer Res* 43, 1809-18.

What is claimed is:

1. An automated method of detecting and enumerating circulating tumor cells in fluids obtained from patients, said method comprising the steps of:
   (i) obtaining a microscope slide having deposited thereon a cell population sample with one or more tumor cells therein, contacted with one or more distinguishable labeled probes directed to one or more characteristic features predetermined to identify a type of tumor cell among normal cells, wherein said contacting is done under conditions sufficient to affix said labeled probe;
   (ii) analyzing said labeled tumor cells on a high-throughput robotic digital microscopy platform programmed to automatically:
      (a) locate said labeled cell at low magnification; followed by
      (b) verification of type of tumor cells bearing at least one said labeled probe at high magnification;
      (c) determine a cell as a type of tumor cell if said labeled probe is detected at high magnification;
      (d) automatically counting normal cells and said type of tumor cells in a field; and
      (e) providing a representation of said type of tumor cells in said normal cell count.

2. The method of claim 1, wherein the type of labeled tumor cell is determined as cancerous or malignant.

3. The method according to claim 1, wherein the determination of type of circulating tumor cells is further aided by designing probes identifying mutations, amplifications or over-expressed receptors, enzyme ligands or other factors affecting disregulated growth.

4. The method according to claim 1, wherein the determination of type of circulating tumor cells is further aids in the design of pharmaceuticals affecting treatment of mutations, amplifications or over-expressed receptors, enzyme ligands or other factors affecting disregulated growth.

5. A method for detecting circulating prostate cancer cells, said method comprising the steps of:
   (i) obtaining a slide carrying peripheral blood from a prostate cancer patient pre-, post, or during, treatment for prostate cancer, the peripheral blood being treated with distinguishable labeled probes directed to one or more characteristic features predetermined to identify malignant cells among normal cells; wherein
      said labeled probes comprise a first, second, third, fourth, and fifth probes directed against a first, second, third, fourth, and fifth characteristic feature of said malignant cells; wherein
      said first probe for epithelial cell marker cytokeratin 7/8 as said first characteristic feature is monoclonal antibody, CAM5.2;
      said second probe for prostate specific antigen as said second characteristic feature is monoclonal antibody, ER-PR8; said third probe for epithelial adhesion molecule EpCam as said third characteristic feature is monoclonal antibody, AUA1;
      said fourth probe for pericentromeric regions of chromosome 7 and 8 as said fourth characteristic feature is chromosome enumeration probe, CEP7;
      said fifth probe for pericentromeric regions of chromosome 17 and 18 as said fifth characteristic feature is chromosome enumeration probe, CEP8; and
      wherein the peripheral blood if further stained with DAPI;
   (ii) analyzing said slide on a high throughput robotic digital microscopy platform programmed to automatically:
      (a) locate cells bearing at least one of said first, second or third probes at low magnification; followed by
      (b) determine any binding of at least one of said fourth probe and said fifth probe at high magnification; and
   (iii) automatically reporting prostate cancer cells if cells are determined to bear at least one of said first, second, and third probes, and at least one of said fourth or fifth probes.

6. The method according to claim 5, wherein the peripheral blood is obtained from said prostate cancer patient after a preoperative biopsy.

7. A method detecting circulating malignant tumor cells associated with ovarian or colorectal cancer comprising the steps of:
   (i) obtaining slide comprising peripheral blood from said ovarian or colorectal cancer patient pre-treatment, post-treatment or concurrent with treatment for said cancer contacted with distinguishable labeled probes directed to one or more characteristic features predetermined to identify malignant tumor cells among normal cells; wherein
      said distinguishable labeled probes comprise a first, second, third, and fourth probes directed against a first, second, third, and fourth characteristic feature of said tumor cell; wherein
      said first probe for epithelial cell marker cytokeratin 7/8 as said first characteristic feature is a monoclonal antibody;
      said second probe for the epithial adhesion molecule EpCam as said second characteristic feature is a monoclonal antibody AUA1;
      said third probe for pericentromeric regions of chromosome 7 and 8 as said third characteristic feature is chromosome enumeration probe CEP7;
      said fourth probe pericentromeric regions of chromosome 17 and 18 as said forth characteristic feature is chromosome enumeration probe CEP8; and wherein the peripheral blood is further stained with DAPI;
   (ii) analyzing said slide on a high throughput robotic digital microscopy platform programmed to automatically:
      (a) locate cells bearing at least one of said first, and second probes at low magnification; followed by
      (b) determine any binding of at least one of said third probe and said fourth probe;
   (iii) automatically reporting ovarian or colorectal malignant cells if the cells are determined to bear at least one of said first and second probes and at least one of said third and fourth probe.

8. The method according to claim 7, wherein the peripheral blood cells were obtained as mononuclear cell populations.

9. The method according to claim 7, wherein the characterization of said tumor cells aids in the anticancer therapy.

* * * * *